(12) United States Patent
Finley et al.

(10) Patent No.: US 12,336,772 B2
(45) Date of Patent: *Jun. 24, 2025

(54) THREE-DIMENSIONAL VISUALIZATION DURING SURGERY

(71) Applicant: NuVasive, Inc., San Diego, CA (US)

(72) Inventors: Eric Finley, San Diego, CA (US);
Kara Robinson, San Diego, CA (US);
DJ Geiger, San Diego, CA (US);
Justin Smith, San Diego, CA (US);
Chris Ryan, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/632,757

(22) Filed: Apr. 11, 2024

(65) Prior Publication Data

US 2024/0261036 A1 Aug. 8, 2024

Related U.S. Application Data

(63) Continuation of application No. 17/520,837, filed as application No. PCT/US2020/032266 on May 9, 2020, now Pat. No. 11,974,819.

(60) Provisional application No. 62/846,319, filed on May 10, 2019.

(51) Int. Cl.
*A61B 34/20* (2016.01)
*A61B 34/10* (2016.01)
*A61B 34/30* (2016.01)

(52) U.S. Cl.
CPC .............. *A61B 34/20* (2016.02); *A61B 34/10* (2016.02); *A61B 2034/102* (2016.02); *A61B 34/30* (2016.02)

(58) Field of Classification Search
CPC ......... A61B 34/20; A61B 34/10; A61B 34/30; A61B 2034/102
See application file for complete search history.

(56) References Cited

PUBLICATIONS

Newell et al, An intraoperative fluoroscopic method to accurately measure the post-implantation position of pedicle screws, Apr. 9, 2018, Springer, International Journal of Computer Assisted Radiology and Surgery (2018) 13:1257-1267 (Year: 2018).*
Intraoperative Fluoroscopic method (Year: 2018).*

\* cited by examiner

*Primary Examiner* — Rochelle D Turchen

(57) ABSTRACT

A method comprising segmenting at least one vertebral body from at least one image of a first three-dimensional image data set. The method comprises receiving at least one image of a second three-dimensional image data set. The method comprises registering the segmented at least one vertebral body from the at least one image of the first three-dimensional image data set with the at least one image of the second three-dimensional image data set. The method comprises determining a position of the at least one surgical implant based on the at least one image of the second three-dimensional image data set and a three-dimensional geometric model of the at least one surgical implant. The method comprises overlaying a virtual representation of the at least one surgical implant on the registered and segmented at least one vertebral body from the at least one image of the first three-dimensional image data set.

6 Claims, 11 Drawing Sheets

THREE-DIMENSIONAL VISUALIZATION DURING SURGERY

CROSS-REFERENCE TO RELATED APPLICATION

This application is a continuation application of U.S. patent Application Ser. No. 17/520,837 which is a U.S. national phase under 35 U.S.C. 371 of international application PCT/US20/32266, filed on May 9, 2020, which claims the benefit of U.S. Provisional Application No. 62/846,319, filed on May 10, 2019, the entire disclosure of which is incorporated herein by reference.

BACKGROUND

Many surgical procedures require obtaining an image of the patient's internal body structure, such as organs and bones. In some procedures, the surgery is accomplished with the assistance of periodic images of the surgical site. Surgery can broadly mean any invasive testing or intervention performed by medical personnel, such as surgeons, interventional radiologists, cardiologists, pain management physicians, and the like. In surgeries, procedures, and interventions that are in effect guided by serial imaging, referred to herein as image guided, frequent patient images are necessary for the physician's proper placement of surgical instruments, be they catheters, needles, instruments or implants, or performance of certain medical procedures. Fluoroscopy, or fluoro, is one form of intraoperative X-ray and is taken by a fluoroscopy unit, also known as a C-Arm. The C-Arm sends X-ray beams through a patient and takes a picture of the anatomy in that area, such as skeletal and vascular structure. It is, like any picture, a two-dimensional (2D) image of a three-dimensional (3D) space. However, like any picture taken with a camera, key 3D info may be present in the 2D image based on what is in front of what and how big one thing is relative to another.

A digitally reconstructed radiograph (DRR) is a digital representation of an X-ray made by taking a CT scan of a patient and simulating taking X-rays from different angles and distances. The result is that any possible X-ray that can be taken for that patient, for example by a C-Arm fluoroscope can be simulated, which is unique and specific to how the patient's anatomical features look relative to one another. Because the "scene" is controlled, namely by controlling the virtual location of a C-Arm to the patient and the angle relative to one another, a picture can be generated that should look like any X-ray taken by a C-Arm in the operating room (OR).

Many imaging approaches, such as taking fluoroscopy images, involve exposing the patient to radiation, albeit in small doses. However, in these image guided procedures, the number of small doses adds up so that the total radiation exposure can be disadvantageous not only to the patient but also to the surgeon or radiologist and others participating in the surgical procedure. There are various known ways to decrease the amount of radiation exposure for a patient/surgeon when an image is taken, but these approaches come at the cost of decreasing the resolution of the image being obtained. For example, certain approaches use pulsed imaging as opposed to standard imaging, while other approaches involve manually altering the exposure time or intensity. Narrowing the field of view can potentially also decrease the area of radiation exposure and its quantity (as well as alter the amount of radiation "scatter") but again at the cost of lessening the information available to the surgeon when making a medical decision. Collimators are available that can specially reduce the area of exposure to a selectable region. However, because the collimator specifically excludes certain areas of the patient from exposure to X-rays, no image is available in those areas. The medical personnel thus have an incomplete view of the patient, limited to the specifically selected area. Further, often times images taken during a surgical intervention are blocked either by extraneous OR equipment or the actual instruments/implants used to perform the intervention.

SUMMARY

In one embodiment, a method comprises segmenting at least one vertebral body from at least one image of a first three-dimensional image data set. The first three-dimensional image data set is based on an initial scan of a surgical site that includes spinal anatomy. The method also comprises receiving at least one image of a second three-dimensional image data set. The second three-dimensional image data set is based on a second scan of the surgical site subsequent to the initial scan of the surgical site. The second scan of the surgical site includes the spinal anatomy and at least one surgical implant. The method also comprises registering the segmented at least one vertebral body from the at least one image of the first three-dimensional image data set with the at least one image of the second three-dimensional image data set. The method also comprises determining a position of the at least one surgical implant based on the at least one image of the second three-dimensional image data set and a three-dimensional geometric model of the at least one surgical implant. The method also comprises based on the determined position of the at least one surgical implant, overlaying a virtual representation of the at least one surgical implant on the registered and segmented at least one vertebral body from the at least one image of the first three-dimensional image data set.

In another embodiment, a method comprises segmenting an image of a first three-dimensional image data set, wherein the first three-dimensional image data set is based on an initial scan of a surgical site that includes spinal anatomy. The method also comprises receiving an image of a second three-dimensional image data set. The second three-dimensional image data set is based on a second scan of the surgical site subsequent to the initial scan of the surgical site. The second scan of the surgical site comprises the spinal anatomy and at least one surgical implant. The method also comprises registering the segmented image of the first three-dimensional image data set with the segmented image of the second three-dimensional image data set. The method also comprises determining a position of the at least one surgical implant based on the at least one image of the second three-dimensional image data set and a three-dimensional geometric model of the at least one surgical implant. The method also comprises based on the determined position of the at least one surgical implant, overlaying a virtual representation of the at least one surgical implant on the registered and segmented image of the first three-dimensional image data set.

In another embodiment, a system for generating a display of an image of a patient's internal anatomy during a surgical procedure comprises a display and a processor in communication with the display. The processor is configured to segment an image of a first three-dimensional image data set. The first three-dimensional image data set is based on an initial scan of a surgical site that includes spinal anatomy.

The processor is also configured to receive an image of a second three-dimensional image data set. The second three-dimensional image data set is based on a second scan of the surgical site subsequent to the initial scan of the surgical site. The second scan of the surgical site includes the spinal anatomy and at least one surgical implant. The processor is also configured to register the segmented image of the first three-dimensional image data set with the image of the second three-dimensional image data set. The processor is also configured to determine a position of the at least one surgical implant based on the image of the second three-dimensional image data set and a three-dimensional geometric model of the at least one surgical implant. The processor is also configured to based on the determined position of the at least one surgical implant, overlay a virtual representation of the at least one surgical implant on the registered and segmented image of the first three-dimensional image data set. The processor is also configured to provide an instruction to display, via the display, the virtual representation of the at least one surgical implant as an overlay onto the registered and segmented image of the first three-dimensional image data set.

DETAILED DESCRIPTION

Figure 1:
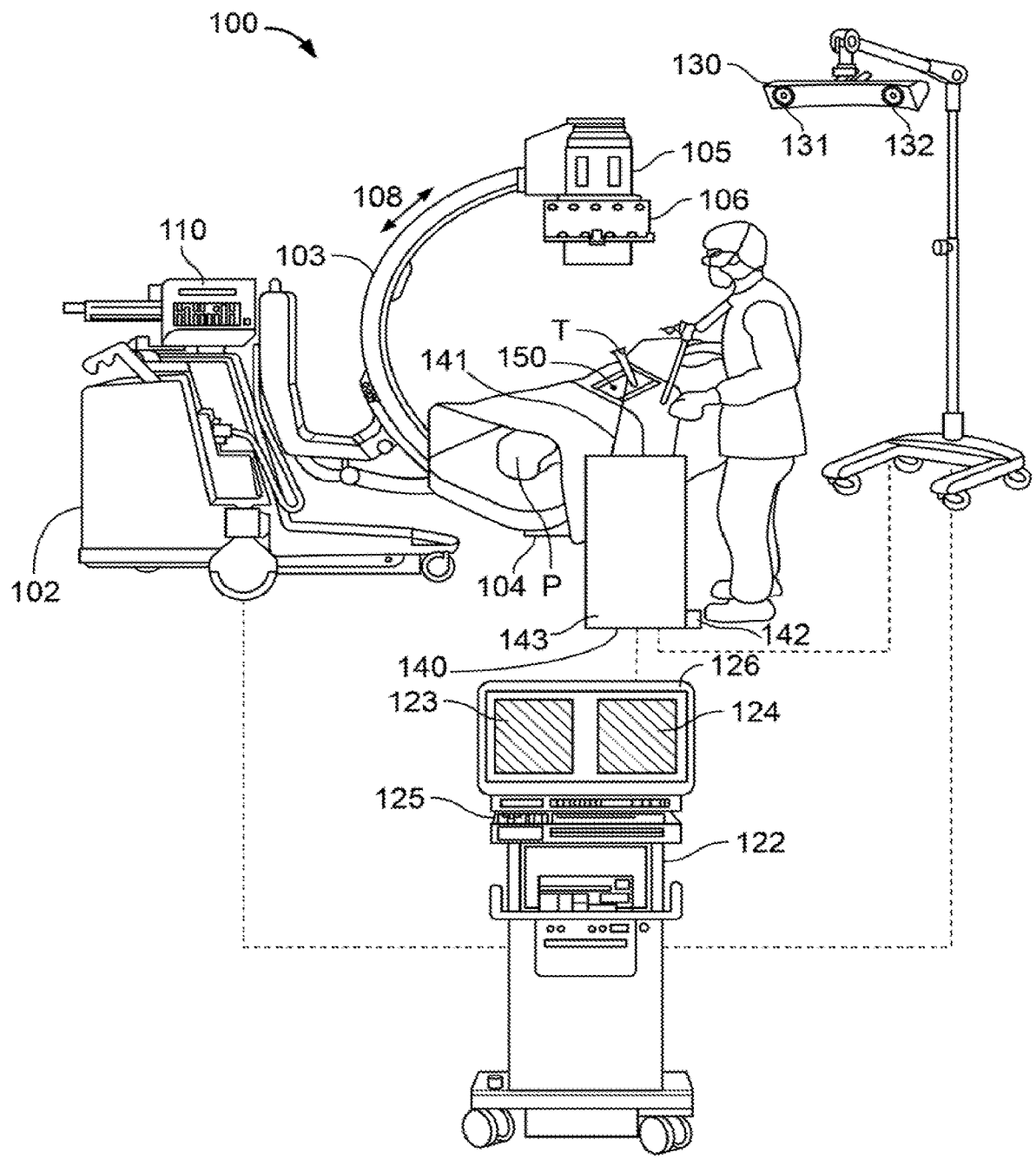
FIG. 1 illustrates a diagram of an example system for performing a surgical procedure, according to an example embodiment.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In one example, a system for generating a display of an image of a patient's internal anatomy during a surgical procedure includes a display and a processor in communication with the display. In one example, the processor is configured to receive a three-dimensional image data set of a surgical site of a patient captured via an imaging device prior to the start of the surgical procedure. The surgical site includes the spinal anatomy of the patient that that is relevant to the surgical procedure. In one scenario, the initial three-dimensional scan of the patient is performed at a higher radiation level than subsequent scans of the patient that are performed intraoperatively to ascertain the progress of the surgical procedure. In one example, the three-dimensional scans are captured via an imaging device such as a C-Arm imaging device.

The processor is also configured to segment an image of a first three-dimensional image data set based on the initial scan of a surgical site that includes spinal anatomy. In one example, the processor may be configured to run one more instructions for segmenting one or more vertebral bodies according to a deep neural network. In one example, the processor is configured to segment the image of the first three-dimensional image data set based on user input via the display. In one example, the user input is received via a touch screen display.

In one scenario, depending on the progression of the surgical procedure, a second scan of the surgical site may be performed to determine if the surgical implant has been inserted according to a surgical plan. In this scenario, the processor is configured to receive an image of a second three-dimensional image data set. The second three-dimensional image data set is based on a second scan of the surgical site subsequent to the initial scan of the surgical site. At the time of the second scan, the surgical site includes the spinal anatomy and at least one surgical implant. In one example, the radiation level corresponding to the second scan is at a lower level than the radiation level corresponding to the initial scan. The lower radiation level will be sufficient to determine the placement of the surgical implant. However, due to the lower radiation level, the resolution of the second three-dimensional image data set may not be sufficient for a user (e.g., surgeon) to determine if the surgical implant has been inserted according to the surgical plan. In order to overcome the resolution of the second three-dimensional image data set, the processor is configured to register the segmented image of the first three-dimensional image data set with the image of the second three-dimensional image data set. The processor is also configured to determine a position of the surgical implant based on one or more imaging algorithms used with the image of the second three-dimensional image data set and a three-dimensional geometric model of the at least one surgical implant. The processor is also configured to overlay a virtual representation of the at least one surgical implant on the registered and segmented image of the first three-dimensional image data set, based on the determined position of the at least one surgical implant. The processor is also configured to provide an instruction to display, via the display, the virtual representation of the at least one surgical implant as an overlay onto the registered and segmented image of the first three-dimensional image data set.

Referring now to the figures, FIG. 1 is a diagram of an example system 100 for performing a surgical procedure and generating a display of an image of a patient's internal anatomy during the surgical procedure. The example system 100 includes a base unit 102 supporting a C-Arm imaging device 103. The C-Arm includes a radiation source 104 that is positioned beneath the patient P and that directs a radiation beam upward to the receiver 105. The receiver 105 of the C-Arm 103 transmits image data to a processing device 122. The processing device 122 may communicate with a tracking device 130 to obtain location information of various instruments T used during the surgical procedure. The tracking device 130 may communicate with a robotic device 140 to provide location information of various tracking elements, such as marker 150. The robotic device 140 and the processing device 122 may communicate via one or more communication channels.

The base unit 102 includes a control panel 110 through which a user can control the location of the C-Arm 103, as well as the radiation exposure. The control panel 110 thus permits the radiology technician to "shoot a picture" of the surgical site at a surgeon's direction, control the radiation dose, and initiate a radiation pulse image.

The C-Arm 103 may be rotated about the patient P in the direction of the arrow 108 for different viewing angles of the surgical site. In one example, the C-Arm 103 is used to capture a three-dimensional scan of the patient. In one example, an initial three-dimensional scan is used to provide a first three-dimensional image data set and second three-dimensional scan is used to provide a second three-dimensional image data set. In one example, the first three-dimensional image data set and the second three-dimensional image data set include one or more of fluoroscopic images or computerized tomography scan images. In another example, the first three-dimensional image data set and the second three-dimensional image data set include fluoroscopic images and the initial scan of the surgical site is associated with a higher radiation level than the second scan of the surgical site. In another example, the second scan includes a plurality of surgical implants associated with the one vertebral body from at least the one image of the first three-dimensional image data set.

In some instances, implants or instruments T may be situated at the surgical site, necessitating a change in viewing angle for an unobstructed view of the site. Thus, the position of the receiver relative to the patient, and more particularly relative to the surgical site of interest, may change during a procedure as needed by the surgeon or radiologist. Consequently, the receiver 105 may include a tracking target 106 mounted thereto that allows tracking of the position of the C-Arm 103 using the tracking device 130. By way of example only, the tracking target 106 may include a plurality of infrared reflectors or emitters spaced around the target, while the tracking device 130 is configured to triangulate the position of the receiver 105 from the infrared signals reflected or emitted by the tracking target 106.

The processing device 122 can include a digital memory associated therewith and a processor for executing digital and software instructions. The processing device 122 may also incorporate a frame grabber that uses frame grabber technology to create a digital image for projection as displays 123 and 124 on a display device 126. The displays 123 and 124 are positioned for interactive viewing by the surgeon during the procedure. The two displays 123 and 124 may be used to show images from two views, such as lateral and A/P, or may show a baseline scan and a current scan of the surgical site. An input device 125, such as a keyboard or a touch screen, can allow the surgeon to select and manipulate the on-screen images. It is understood that the input device may incorporate an array of keys or touch screen icons corresponding to the various tasks and features implemented by the processing device 122. The processing device 122 includes a processor that converts the image data obtained from the receiver 105 into a digital format. In some cases, the C-Arm 103 may be operating in the cinematic exposure mode and generating many images each second. In these cases, multiple images can be averaged together over a short time period into a single image to reduce motion artifacts and noise.

In one example, once the initial three-dimensional scan is acquired, a three-dimensional image data set is generated in which a three-dimensional image is digitally rotated, translated and resized to create thousands of permutations of the three-dimensional image. For example, a typical two-dimensional (2D) image of 128.times.128 pixels may be translated .+-.15 pixels in the x and y directions at 1 pixel intervals, rotated .+-.9.degree. at 3.degree. intervals and scaled from 92.5% to 107.5% at 2.5% intervals (4 degrees of freedom, 4D), yielding 47,089 images in the image data set. A three-dimensional (3D) image will imply a 6D solution space due to the addition of two additional rotations orthogonal to the x and y axis. An original computerized tomography image data set can be used to form many thousands of digitally reconstructed radiographs in a similar fashion. Thus, the original three-dimensional image spawns thousands of new image representations as if the initial three-dimensional image was acquired at each of the different movement permutations. This "solution space" may be stored in a graphics card memory, such as in the graphics processing unit (GPU) of the processing device 122, or formed as a new image which is then sent to the GPU, depending on the number of images in the solution space and the speed at which the GPU can produce those images.

During a surgical procedure, a new three-dimensional image is acquired at a lower dose of radiation and stored in the memory associated with the processing device 122. Since the new image is obtained at a lower dose of radiation it may be very noisy. In one example, the processing device 122 is configured to "merge" the new image with a segmented image from the initial three-dimensional image data set to produce a clearer image for display that conveys more useful information to a user (e.g., surgeon). The new image is compared to the images in the initial three-dimensional image data set to find a statistically meaningful match.

In one example, an image registration occurs in less than one second so that there is no meaningful delay between when the image is taken by the C-Arm 103 and when the merged image is shown on the display device 126. Various algorithms may be employed that may be dependent on various factors, such as the number of images in the initial three-dimensional image data set, the size and speed of the computer processor or graphics processor performing the algorithm calculations, the time allotted to perform the computations, and the size of the images being compared (e.g., 128.times.128 pixels, 1024.times.1024 pixels, etc.). In one approach, comparisons are made between pixels at predetermined locations described above in a grid pattern throughout 4D or 6D space. In another heuristic approach, pixel comparisons can be concentrated in regions of the images believed to provide a greater likelihood of a relevant match. These regions may be "pre-seeded" based on knowledge from a grid or PCA search (defined below), data from a tracking system (such as an optical surgical navigation device), or location data from the DICOM file or the equivalent. Alternatively, the user can specify one or more regions of the image for comparison by marking on the initial three-dimensional image the anatomical features considered to be relevant to the procedure. With this input each pixel in the region can be assigned a relevance score between 0 and 1 which scales the pixel's contribution to the image similarity function when a new image is compared to the initial three-dimensional image. The relevance score may be calibrated to identify region(s) to be concentrated on or region(s) to be ignored. In one example, registering a segmented image of the first three-dimensional image data set with the image of the second three-dimensional image data set includes one or more of a horizontal translation, a vertical translation, a rotation, and a scaling of the image information contained within the one vertebral body from the at least one image of the first three-dimensional image data set.

The tracking device 130 includes sensors 131 and 132 for determining location data associated with a variety of elements (e.g., an infrared reflector or emitter) used in a surgical procedure. In one example, the sensors 131 and 132 may be a charge-coupled device (CCD) image sensor. In another example, the sensors 131 and 132 may be a complementary metal-oxide-semiconductor (CMOS) image sensor. It is also envisioned that other image sensors may be used to achieve the functionality described.

In one aspect of the present invention, the robotic device 140 may assist with holding an instrument T relative to the patient P during a surgical procedure. In one scenario, the robotic device 140 may be configured to maintain the instrument T in a position relative to the patient P as the patient P moves (e.g., due to breathing) or is moved (e.g., due to manipulation of the patient's body) during the surgical procedure.

The robotic device 140 may include a robot arm 141, a pedal 142, and a mobile housing 143. The robotic device 140 may also be in communication with a display 126. The robotic device 140 may also be configured to be coupled to an operating table by a fixation device.

The robot arm 141 may be configured to receive one or more end effectors depending on the surgical procedure. In one example, the robot arm 141 may be a six joint arm. In this example, each joint includes an encoder which measures its angular value. The movement data provided by the one or more encoders, combined with the known geometry of the six joints, may allow for the determination of the position of the robot arm 141 and the position of the instrument T coupled to the robot arm 141. It also envisioned that a different number of joints may be used to achieve the functionality described herein.

The mobile housing 143 ensures easy handling of the robotic device 140 through the use of wheels or handles or both. In one embodiment, the mobile base may include immobilization pads or an equivalent device. The mobile housing 143 may also include a control unit which provides one or more commands to the robot arm 141 and allows a surgeon to manually input data through the use of an interface, such as a touch screen, a mouse, a joystick, a keyboard or similar device.

Figure 2:
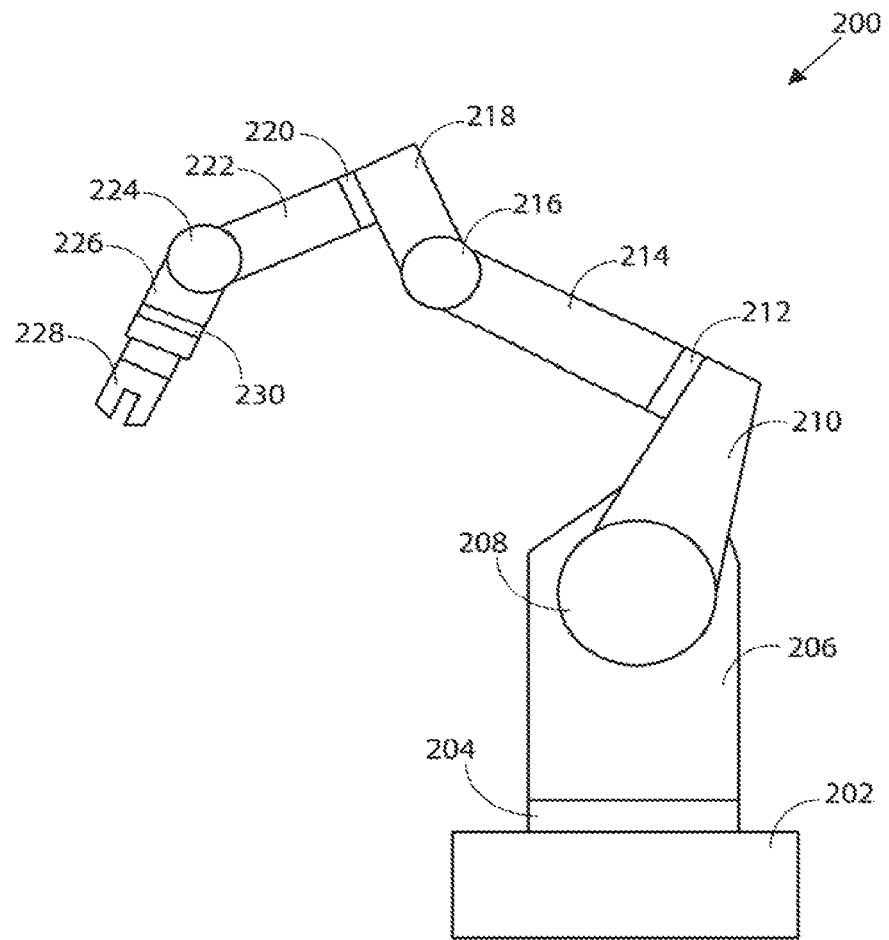
FIG. 2 illustrates an example robotic device that may be used during a surgical procedure, according to an example embodiment.

FIG. 2 illustrates an example robotic device 200 that may be used during a surgical procedure. The robotic device 200 may contain hardware, such as a processor, memory or storage, and sensors that enable the robotic device 200 to operate the robotic device for use in a surgical procedure. The robotic device 200 may be powered by various means such as electric motor, pneumatic motors, hydraulic motors, etc. The robotic device 200 includes a base 202, links 206, 210, 214, 218, 222, and 226, joints 204, 208, 212, 216, 220, 224 and 230, and manipulator 228.

The base 202 may provide a platform in order to provide support for the robotic device 200. The base 202 may be stationary or be coupled to wheels in order to provide movement of the robotic device 200. The base may comprise any number of materials such as aluminum, steel, stainless steel, etc., that may be suitable for a given environment associated with the robotic device 200.

The links 206, 210, 214, 218, 222, and 226 may be configured to be moved according to a programmable set of instructions. For instance, the links may be configured to follow a predetermined set of movements in order to accomplish a task under the supervision of a user. By way of example, the links 206, 210, 214, 218, 222, and 226 may form a kinematic chain that defines relative movement of a given link of links 206, 210, 214, 218, 222, and 226 at a given joint of the joints 204, 208, 212, 216, 220, 224, and 230.

The joints 204, 208, 212, 216, 220, 224, and 230 may be configured to rotate through the use of a mechanical gear system. In one example, the mechanical gear system may be driven by a strain wave gearing, a cycloid drive, etc. The mechanical gear system selected would depend on a number of factors related to the operation of the robotic device 200 such as the length of the given link of the links 206, 210, 214, 218, 222, and 226, speed of rotation, desired gear reduction, etc. Providing power to the joints 204, 208, 212, 216, 220, 224, and 230 will allow for the links 206, 210, 214, 218, 222, and 226 to be moved in a way that allows the manipulator 228 to interact with an environment.

The manipulator 228 may be configured to allow the robotic device 200 to interact with the environment. In one example, the manipulator 228 may perform appropriate placement of an element through various operations such as gripping a surgical instrument. By way of example, the manipulator may be exchanged for another end effector that would provide the robotic device 200 with different functionality.

The robotic device 200 may be configured to operate according to a robot operating system (e.g., an operating system designed for specific functions of the robot). A robot operating system may provide libraries and tools (e.g., hardware abstraction, device drivers, visualizers, message-passing, package management, etc.) to enable robot applications.

Figure 3:
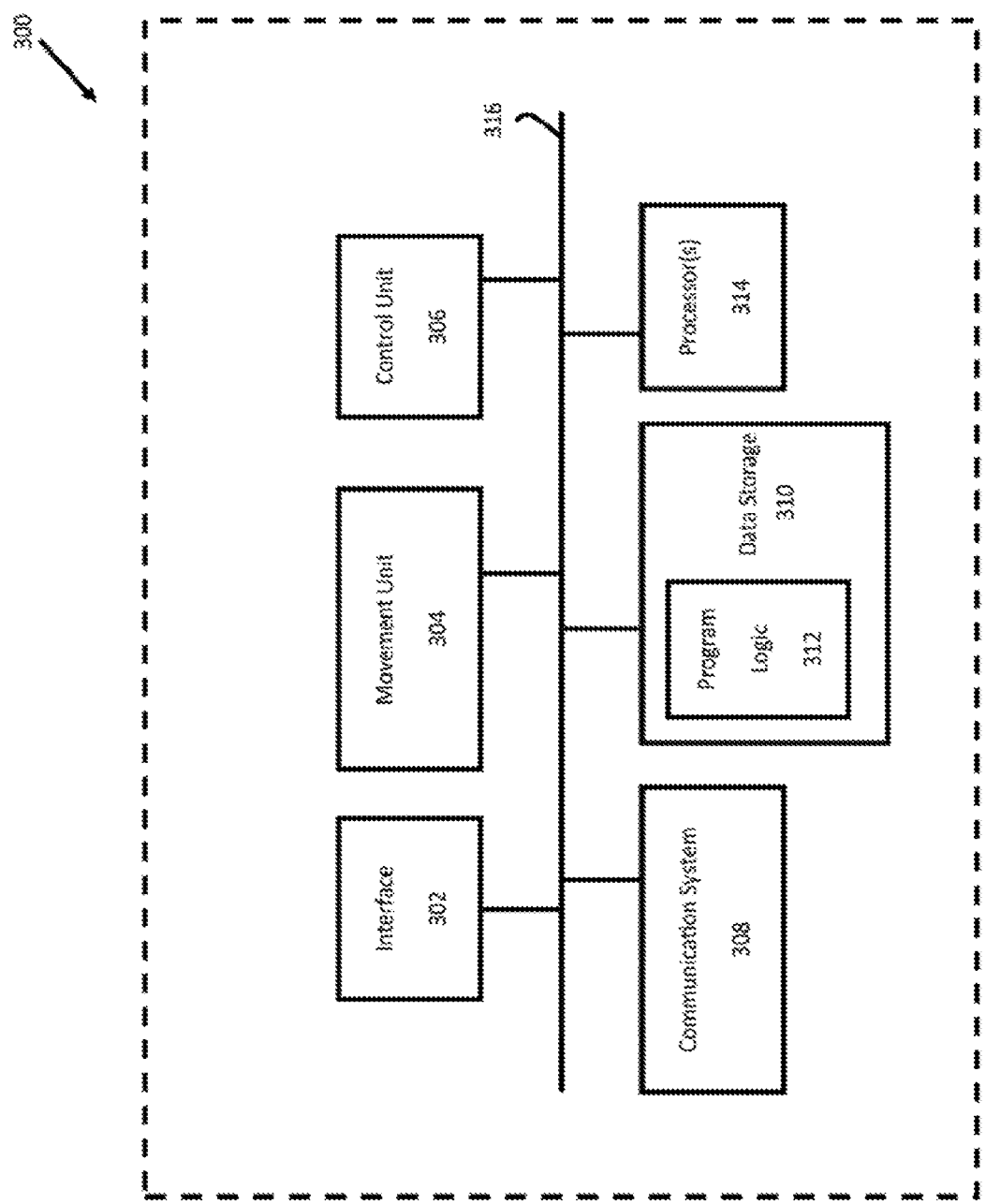
FIG. 3 illustrates a block diagram of a computing device, according to an example embodiment.

FIG. 3 is a block diagram of a computing device 300, according to an example embodiment. In some examples, some components illustrated in FIG. 3 may be distributed across multiple computing devices (e.g., desktop computers, servers, hand-held devices, etc.). However, for the sake of the example, the components are shown and described as part of one example device. The computing device 300 may include an interface 302, a movement unit 304, a control unit 306, a communication system 308, a data storage 310, and a processor 314. Components illustrated in FIG. 3 may be linked together by a communication link 316. In some examples, the computing device 300 may include hardware to enable communication within the computing device 300 and another computing device (not shown). In one embodiment, the robotic device 140 or the robotic device 200 may include the computing device 300.

The interface 302 may be configured to allow the computing device 300 to communicate with another computing device (not shown). Thus, the interface 302 may be configured to receive input data from one or more devices. In some examples, the interface 302 may also maintain and manage data received and sent by the computing device 300. In other examples, data may be maintained and managed by other components of the computing device 300. The interface 302 may also include a receiver and transmitter to receive and send data. In some examples, the interface 302 may also include a user-interface, such as a keyboard, microphone, touch screen, etc., to receive inputs as well. Further, in some examples, the interface 302 may also interface with output devices such as a display, speaker, etc.

By way of example, the interface 302 may receive an input indicative of a location information corresponding to one or more elements of an environment in which a robotic device (e.g., robotic device 140, robotic device 200) resides. In this example, the environment may be an operating room in a hospital comprising the robotic device that is configured to function during a surgical procedure. The interface 302 may also be configured to receive information associated with the robotic device. For instance, the information associated with the robotic device may include operational characteristics of the robotic device and a range of motion with a component of the robotic device.

The control unit 306 of the computing device 300 may be configured to run control software which exchanges data with elements (e.g., robot arm 141, robot pedal 142, joints 204, 208, 212, 216, 220, 224, and 230, manipulator 228, etc.) of a robotic device (e.g., robotic device 140, robotic device 200) and one or more other devices (e.g., processing device 122, tracking device 130, etc.). The control software may communicate with the user through a user interface and display monitor (e.g., display 126) in communication with the robotic device. The control software may also communicate with the tracking device 130 and the processing device 122 through a wired communication interface (e.g., parallel port, USB, etc.) and/or a wireless communication interface (e.g., antenna, transceivers, etc.). The control software may communicate with one or more sensors to measure the efforts exerted by the user at the instrument T mounted to a robot arm (e.g., robot arm 141, link 226). The control software may communicate with the robot arm to control the position of the robot arm relative to a marker (e.g., marker 150).

As described above, the control software may be in communication with the tracking device 130. In one scenario, the tracking device 130 may be configured to track the marker 150 that is attached to the patient P. By way of example, the marker 150 may be attached to a spinous process of a vertebra of the patient P. In this example, the marker 150 may include one or more infrared reflectors that are visible to the tracking device 130 to determine the location of the marker 150. In another example, multiple markers may be attached to one or more vertebrae and used to determine the location of the instrument T.

In one example, the tracking device 130 may provide updates in near real-time of the location information of the marker 150 to the control software of the robotic device 140. The robotic device 140 may be configured to receive updates to the location information of the marker 150 from the tracking device 130 via a wired and/or wireless interface. Based on the received updates to the location information of the marker 150, the robotic device 140 may be configured to determine one or more adjustments to a first position of the instrument T in order to maintain a desired position of the instrument T relative to the patient P.

The control software may include independent modules. In an exemplary embodiment, these independent modules run simultaneously under a real time environment and use a shared memory to ensure management of the various tasks of the control software. The modules may have different priorities, such as a safety module having the highest priority, for example. The safety module may monitor the status of the robotic device 140. In one scenario, the safety module may send an instruction to the control unit 306 to stop the robot arm 141 when a critical situation is detected, such as an emergency stop, software failure, or collision with an obstacle, for example.

The control unit 306 may be configured to manage the functions associated with various components (e.g., robot arm 141, pedal 142, etc.) of the robotic device 140. For example, the control unit 306 may send one or more commands to maintain a desired position of the robot arm 141 relative to the marker 150. The control unit 306 may be configured to receive movement data from a movement unit 304.

The movement unit 304 may be configured to determine the movement associated with one or more components of the robot arm 141 to perform a given procedure. In one embodiment, the movement unit 304 may be configured to determine the trajectory of the robot arm 141 using forward and inverse kinematics. In one scenario, the movement unit 304 may access one or more software libraries to determine the trajectory of the robot arm 141.

The movement unit 304 may be configured to simulate an operation of the robotic device 140 moving an instrument T along a given path. In one example, based on the simulated operation, the movement unit 304 may determine a metric associated with the instrument T. Further, the movement unit 304 may be configured to determine a force associated with the metric according to the simulated operation. In one example, the movement unit 304 may contain instructions that determine the force based on an open kinematic chain.

The movement unit 304 may include a force module to monitor the forces and torques measured by one or more sensors coupled to the robot arm 141. In one scenario, the force module may be able to detect a collision with an obstacle and alert the safety module.

An interface 302 may be configured to allow the robotic device 140 to communicate with other devices (e.g., processing device 122, tracking device 130). Thus, the interface 302 may be configured to receive input data from one or more devices. In some examples, the interface 302 may also maintain and manage records of data received and sent by other devices. In other examples, the interface 302 may use a receiver and transmitter to receive and send data.

The interface 302 may be configured to manage the communication between a user and control software through a user interface and display screen (e.g., via displays 123 and 124). The display screen may display a graphical interface that guides the user through the different modes associated with the robotic device 140. The user interface may enable the user to control movement of the robot arm 141 associated with the beginning of a surgical procedure, activate a tracking mode to be used during a surgical procedure, and stop the robot arm 141 if needed, for example.

In one example, a user may control actuation of the robot arm 141 through the use of a robot pedal 142. In one embodiment, the user may depress the robot pedal 142 to activate one or more modes of the robotic device 140. In one scenario, the user may depress the robot pedal 142 to allow the user to manually position the robot arm 141 according to a desired position. In another scenario, the user may depress the robot pedal 142 to activate a tracking mode that enables the robot arm 141 to maintain an instrument T in a relative position to the patient P. In another scenario, the user may depress the robot pedal 142 to stop the robot arm 141 from proceeding with any further movements.

In one scenario, the control unit 306 can instruct the robot arm 141 to function according to a cooperative mode. In the cooperative mode, a user is able to move the robot arm 141 manually by holding the tool T coupled to the robot arm 141 and moving the instrument T to a desired position. In one example, the robotic device 140 may include one or more force sensors coupled to an end effector of the robot arm 141. By way of example, when the user grabs the instrument T and begins to move it in a direction, the control unit 306 receives efforts measured by the force sensor and combines them with the position of the robot arm 141 to generate the movement desired by the user.

In one scenario, the control unit 306 can instruct the robot arm 141 to function according to a tracking mode. In the tracking mode, the robotic device 140 will maintain a relative position of the instrument T to a given IR reflector or emitters (e.g., the marker 150). In one example, the robotic device 140 may receive updated position information of the marker 150 from the tracking device 130. In this example, the movement unit 304 may determine, based on the received updated position information of the marker 150, which joint(s) of the robot arm 141 need to move in order to maintain the relative position of the instrument T with the marker 150.

In one embodiment, the robotic device 140 may be in communication with the processing device 122. In one example, the robotic device 140 may provide the location information of the instrument T to the processing device 122. In this example, the processing device 122 may be configured to store the location information of the instrument T for further processing. In one scenario, the processing device 122 may use the received location of the instrument T to overlay a virtual representation of the instrument T on display 126.

In another aspect of the present invention, a robotic device (e.g., robotic device 140, robotic device 200) may assist with movement of an instrument along a planned or learned path. In one scenario, the surgeon may plan for a trajectory of a pedicle screw or placement of a retractor either pre-operatively based on three-dimensional (3D) imagery or intra-operatively by holding a position outside the skin and seeing how the trajectory intersects the anatomy of concern by projecting an instrument's tip into the patient.

In one scenario, the surgeon may pre-operatively choose the ideal pedicle screw trajectory for a specific level of the spine, but then choose a different trajectory to penetrate the skin and muscle intra-operatively. In one example, the surgeon may guide the tool coupled to the robotic device along a different trajectory until the tool intersects with an ideal pedicle screw trajectory. In this example, the robotic device may provide a signal to a computing device (e.g., processing device 122, computing device 300) which in turn could notify the surgeon via an audible or visual alert that the ideal pedicle screw trajectory has been reached.

In another scenario, once the instrument coupled to a robot arm (e.g., robot arm 141, links 206, 210, 214, 218, 222, and 226) of a robotic device reaches the ideal pedicle screw trajectory, the robotic device may be configured to receive an input from the surgeon to travel along the ideal pedicle screw. In one example, the surgeon may provide an input to the robotic device (e.g., depressing the pedal 142) to confirm the surgeon's desire to enable the robotic device to travel along the ideal pedicle screw. In another example, a user may provide another form of input to either the robotic device or the computing device to assist with movement of an instrument along a predetermined path.

In one scenario, once the robotic device has received confirmation to travel along the ideal pedicle screw trajectory, the robotic device may receive instructions from the movement unit 304 to pivot from the current trajectory to the ideal pedicle screw trajectory. The movement unit 304 may provide the control unit 306 the required movement data to enable the robotic device to move along the ideal pedicle screw trajectory.

In another example, the movement unit 304 may provide one or more trajectories to a computing device (e.g., processing device 122) for display on display 126. In this example, a user may choose from one or more predetermined movements associated with a given procedure. For example, a given predetermined movement may be associated with a specific direction and amount of movement to be performed through the use of depressing the pedal 142 of the robotic device 140.

In another aspect of the present invention, one or more infrared (IR) reflectors or emitters may be coupled to a robot arm (e.g., robot arm 141, links 206, 210, 214, 218, 222, and 226) of the robotic device (e.g., robotic device 140, robotic device 200). In one scenario, the tracking device 130 may be configured to determine the location of the one or more IR reflectors or emitters prior to beginning operation of the robotic device. In this scenario, the tracking device 130 may provide the location information of the one or more IR reflectors or emitters to a computing device (e.g., processing device 122, computing device 300).

In one example, the processing device 122 or computing device 300 may be configured to compare the location information with data stored on a local or remote database that contains information about the robotic device (e.g., a geometric model of the robotic device) to assist in determining a location or position of the robot arm. In one example, the processing device 122 may determine a first position of the robot arm from information provided by the tracking device 130. In this example, the processing device 122 may provide the determined first position of the robot arm to the robotic device or a computing device (e.g., computing device 300). In one example, the robotic device may use the received first position data to perform a calibration of one or more elements (e.g., encoders, actuators) associated with the one or more joints of the robot arm.

In one scenario, an instrument coupled to the robot arm of the robotic device may be used to determine a difference between an expected tip location of the instrument and the actual tip location of the instrument. In this scenario, the robotic device may proceed to move the instrument to a known location by the tracking device 130 so that the tip of the tool is in contact with the known location. The tracking device 130 may capture the location information corresponding to the one or more IR reflectors or emitters coupled to the robot arm and provide that information to the robotic device or a computing device (e.g., processing device 122, computing device 300). Further, either the robotic device or the computing device may be configured to adjust a coordinate system offset between the robotic device and the tracking device 130 based on an expected tip location of the tool and the actual tip location of the tool.

In one example, the surgeon may incorporate the use of a three-dimensional image of the spine and define one or more planes that the instrument should not traverse. In this example, despite the force or pressure sensor detecting a force to move the instrument, the robot arm will not allow the surgeon to move the instrument past the defined one or more planes according to the constraints associated with the predefined plan. By way of example, the robotic device may be configured to provide an alert to the surgeon as the instrument approaches the one or more restricted planes.

In another aspect of the present invention, a robotic device (e.g., robotic device 140, robotic device 200) may be used to navigate one or more surgical instruments and implants. The robotic device may be configured to provide the navigation information to a computing device (e.g., processing device 122, computing device 300) for further processing. In one example, the computing device may be configured to determine a virtual representation of the surgical instrument or the implant. Further, the computing device may be configured to overlay the virtual representation of the surgical instrument or the implant on a two-dimensional or three-dimensional image of the surgical site.

In one example, the robotic device may perform a calibration procedure between the tracking device 130 in order to remove the dependence on the tracking device 130 for location information in the event that a line of sight between the robotic device and the tracking device 130 is blocked. In one example, using a robotic device which has been registered to a navigation system, as described above, and a patient's three-dimensional image that corresponds to the surgical site may allow the robotic device to become independent of the degradation of accuracy with distance associated with the tracking device 130.

In another example, the robotic device may be used in one or more surgical procedures where the anatomy of the patient is oriented in a way that limits the ability for the tracking device 130 to maintain a line of sight with the anatomy. By way of example, the tracking device 130 may have difficulty maintaining a line of sight during a single position surgery.

In one example, the robot arm of the robotic device may be coupled to an end effector that is configured to attach to the spinous process of a vertebra of the patient. The end effector may include one or more force or pressure sensors to detect an amount of force or pressure exerted by the spinous process during the surgical procedure. This would enable the robotic device to transmit location or position information associated with movement of the patient to a computing device (e.g., processing device 122, computing device 300). In one scenario, the computing device may be configured to receive the location or position information associated with movement of the patient and update one or more images of the surgical site based on the movement information. For example, the computing device may access a database containing a baseline image set of the surgical site and provide an image for display on display 126 that corresponds to the updated position of the patient based on the received position information from the robotic device while the end effector is attached the spinous process. One advantage of using the robotic device to track the movement of the patient is dispensing with the need to attach one or more IR reflective markers to the spinous process to track movements of the patient via the tracking device 130.

In another example, the robotic device may assist with tracking instruments coupled to the robot arm in one or more locations during a surgical procedure. Tracking the instruments via the movement of the robotic device may enable the instrument to be placed in a location that is difficult for a surgeon to see. For example, the instrument may be placed behind a drape but tracked via the robotic device and a computing device (e.g., processing device 122, computing device 300). In another example, the robotic device may assist with tracking the movements of the patient under a sterile barrier. In this example, the robotic device may be used to reposition a bed to keep the patient in a known orientation during a surgical procedure.

In one example, the surgeon may input the path of the surgical procedure prior to beginning the surgical procedure. For example, the surgeon may use a two-dimensional or three-dimensional image of the patient's anatomy and determine a path for reaching a surgical site. In one example, a computing device (e.g., processing device 122, computing device 300) may store information corresponding to the predetermined path and provide the information to the robotic device prior to the beginning of the surgical procedure. Once the robotic device is aware of the position of the robotic device relative to the patient, the movement unit 304 may use the information corresponding to the predetermined path to determine one or more trajectories allowed.

In another example, a path limiting the movement of robot arm may correspond to one or more inputs corresponding to anatomical segmentation. For example, a surgeon may select a particular vertebra to limit the movements of the robot arm to that particular vertebra. By way of example, the robotic device may be further instructed to limit the movement of the robot arm to a specific portion of a vertebra (e.g., the spinous process, etc.).

In one embodiment, an end effector may be coupled to a robot arm (e.g., robot arm 141, links 206, 210, 214, 218, 222, and 226) and assist with placement of a fastener. In one scenario, the robotic device may receive three-dimensional geometric information about a plate and fastener(s) being used in a surgical procedure from a computing device (e.g., processing device 122, computing device 300).

In one example, a given plate may require four fasteners to be installed during a surgical procedure. In this example, the robotic device may use the end effector to retract the soft tissue that corresponds to a first fastener position of the given plate based on a trajectory determined by the movement unit 304. Further, the movement unit 304 may also be configured to determine an optimal trajectory for placement of the fastener through the given plate. Following the placement of the first fastener, the robotic device may be configured to move the end effector in a manner that allows for the soft tissue to return to its original position and move to retract the soft tissue that corresponds to a second fastener position of the given plate. In this example, the robotic device may minimize the time that the soft tissue is retracted and thereby decrease a risk to damaging the soft tissue while installing each of the fasteners to the given plate.

In another aspect of the present invention, a robotic device (e.g., robotic device 140, robotic device 200) may use location information captured by the tracking device 130 to determine the position of an instrument and implants coupled to a robot arm (e.g., robot arm 141, links 206, 210, 214, 218, 222, and 226) relative to the patient. In one embodiment, the robotic device may use movement information determined by encoders associated with one or more joints (e.g., joints 204, 208, 212, 216, 220, 224, and 230) of the robotic device to determine the position of the surgical tool after a calibration procedure between the robotic device and the tracking device 130. In another embodiment, the tracking device 130 may provide location information to a computing device (e.g., processing device 122, computing device 300) to assist with tracking the robotic device during the surgical procedure.

In one example, the tracking device 130 may track the position of the instrument coupled to the robot arm based on one or more IR reflectors or emitters. For example, the tracking device 130 may detect the IR reflectors or emitters coupled to the tool and provide location information to the processing device 122. The processing device 122 may be configured to compare the last known position information of the IR reflectors or emitters coupled to the instrument with the most recent position information and determine a change in position associated with the instrument.

In another example, a virtual representation of the path associated with the instrument coupled to the robot arm may be overlaid on the corresponding locations of the patient's anatomy. The virtual representation of the path may be displayed with a variety of visual effects to denote multiple passes by the instrument over a particular area of the spine.

In another aspect of the present invention, the robotic device (e.g., robotic device 140, robotic device 200) may include more than one robot arm (e.g., robot arm 141, links 206, 210, 214, 218, 222, and 226). In one scenario, as described above, the robotic device and the tracking device 130 may have completed a registration process to correct any offset between each of their coordinate systems. In this scenario, in addition to completion of the registration process, the processing device 122 may be configured to receive a three-dimensional scan of the spine of the patient. In one embodiment, the robotic device may be configured to maintain a spinal alignment of the patient according to a preoperative plan for spinal alignment.

In one example, the robotic device may use an end effector that is configured for gripping a critical element of the surgical procedure. For example, the robotic device may use a first gripper coupled to the robot arm to grip a first pedicle screw and a second gripper coupled to a second robot arm to grip a second pedicle screw. The robotic device may be configured to provide a computing device (e.g., processing device 122, computing device 300) the position information associated with each of the first and second robot arms. Based on the received position information, the computing device may determine a current spinal alignment. Further, the computing device may analyze the current spinal alignment to determine a required correction of the spine during a surgical procedure.

In another aspect of the present invention, the robot arm (e.g., robot arm 141, links 206, 210, 214, 218, 222, and 226) of the robotic device (e.g., robotic device 140, robotic device 200) may be configured to receive an ultrasonic probe. In one scenario, the ultrasonic probe is held by the robot arm in a known orientation so that it registers the location of the anatomy in the image for subsequent instrumentation relative to the image with either the robot arm or a co-registered navigation system (e.g., registration between robotic device 140 or robotic device 200 and tracking device 130).

Figure 4:
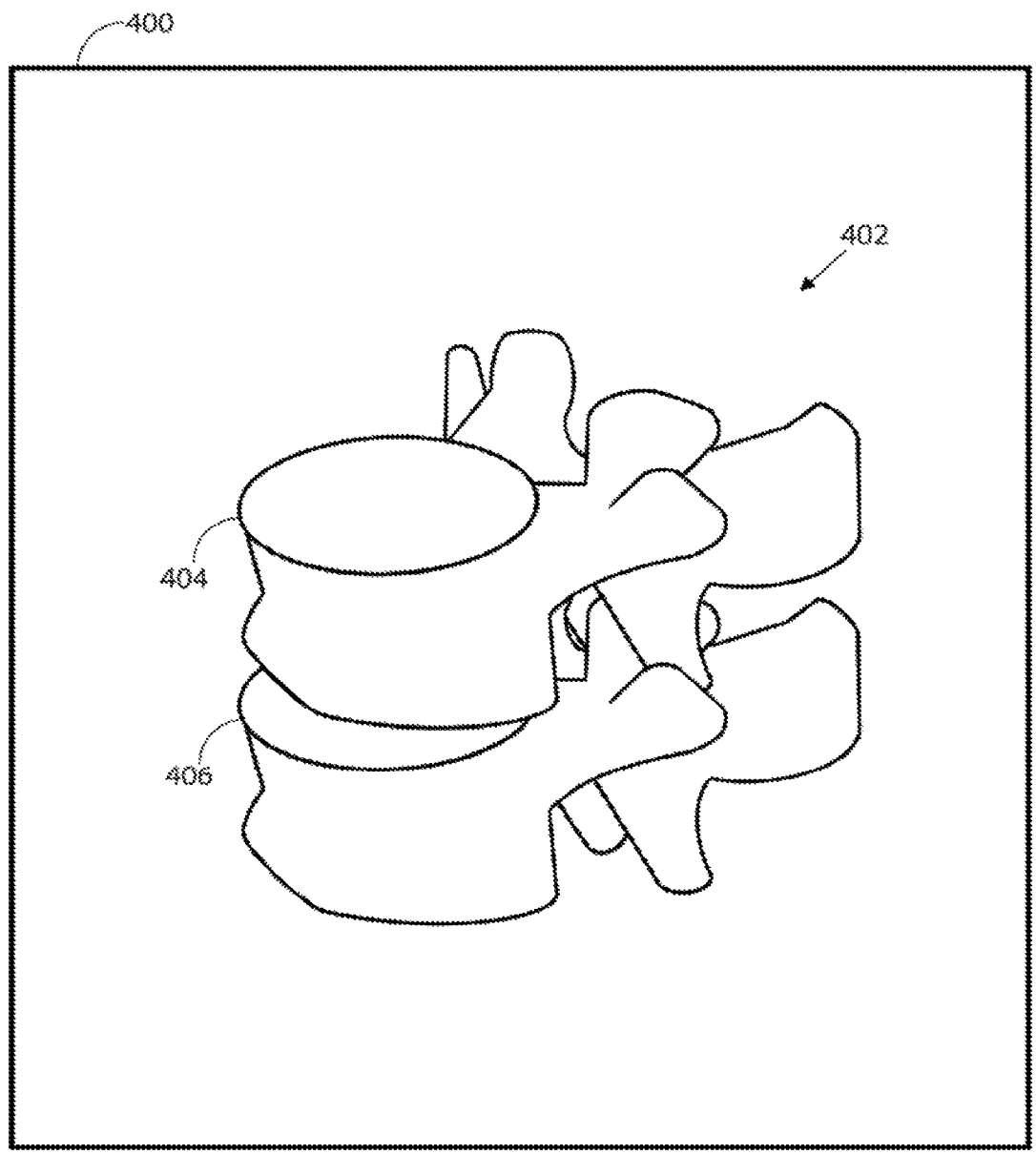
FIG. 4 illustrates an example diagram of an image from a three-dimensional image data set, according to an example embodiment.
Figure 5:
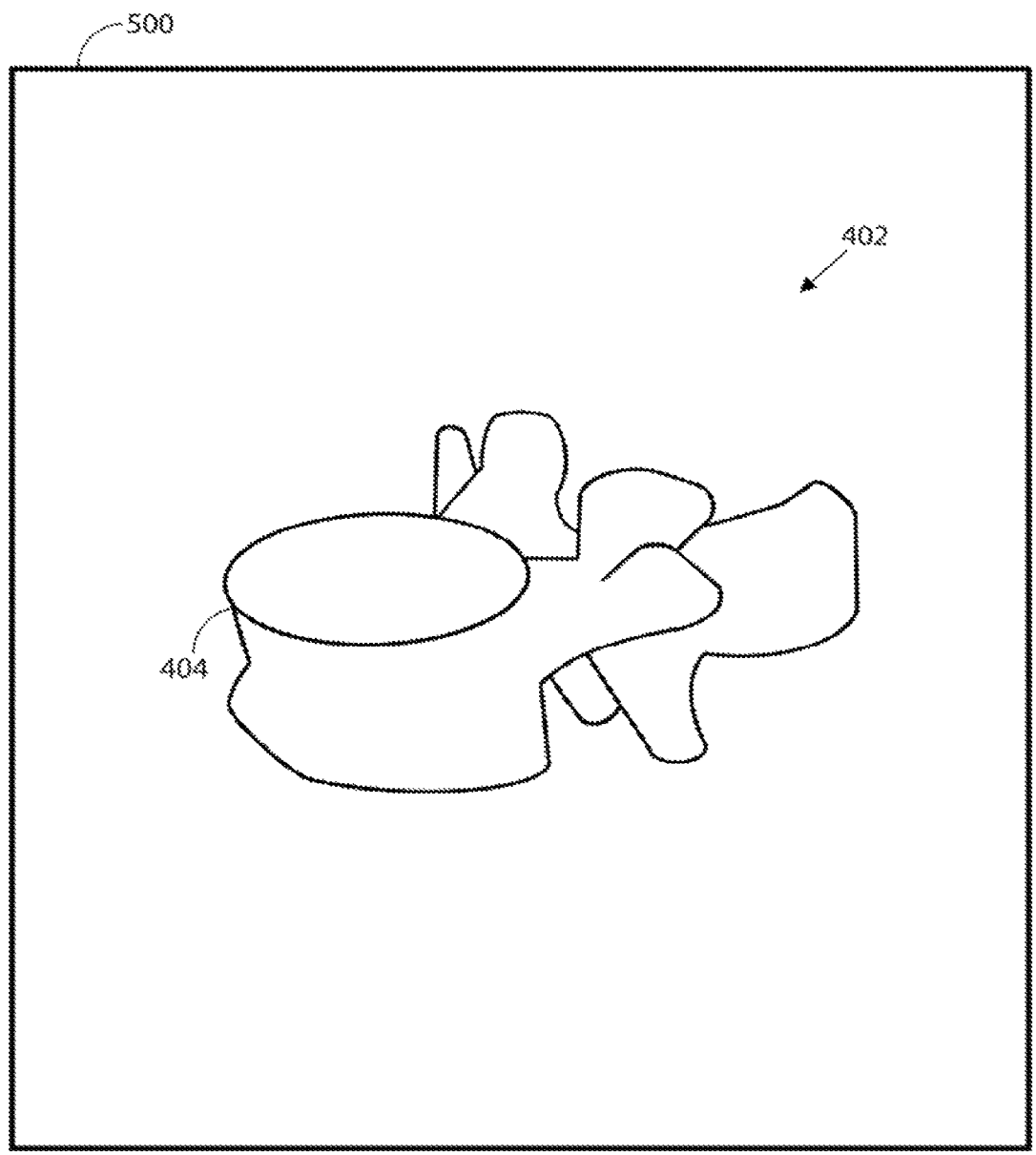
FIG. 5 illustrates an example diagram of another image, according to an example embodiment.

FIG. 4 is an example diagram of an image 400 from a three-dimensional image data set based on an initial scan of a surgical site 402 that includes spinal anatomy. In one example, the initial scan of the surgical site 402 may be performed by the C-Arm imaging device 103 of FIG. 1 prior to the start of a surgical procedure. The image 400 includes a first vertebral body 404 and a second vertebral body 406. In one example, the processing device 122 of FIG. 1 is configured to segment the first vertebral body 404 from the image 400. For example, FIG. 5 is an example diagram of an image 500 that includes the first vertebral body 404 segmented from the second vertebral body 406.

Figure 6:
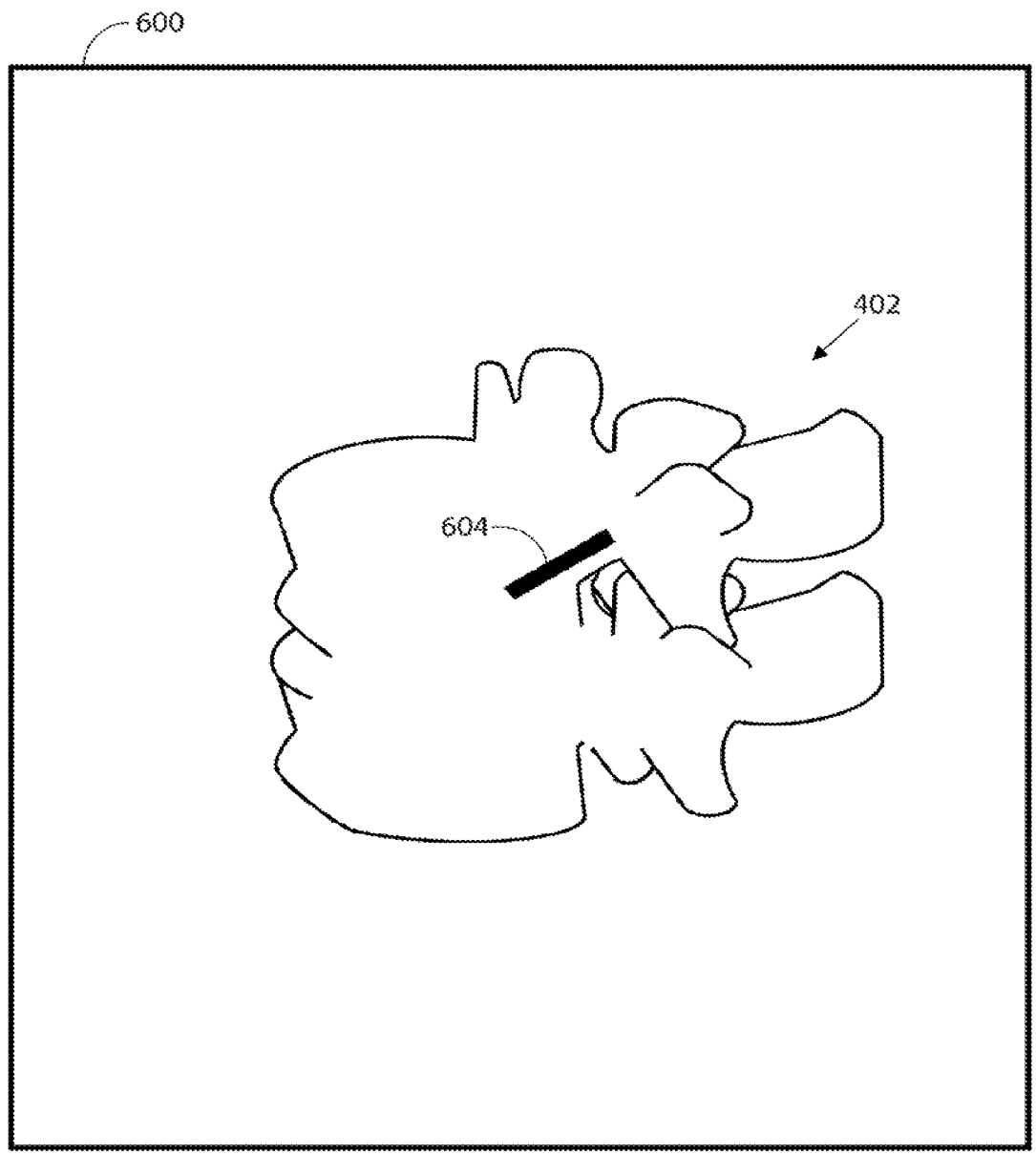
FIG. 6 illustrates an example diagram of another image from a second three-dimensional image data set, according to an example embodiment.

In one example during a given surgical procedure, one or more surgical implants (e.g., pedicle screws) may be inserted into the first vertebral body 404 in order to achieve a given surgical outcome. In this example, after the one or more surgical implants are inserted into the first vertebral body 404, a user (e.g., a surgeon) may want to review the positioning of the implants. In one example, a second scan of the surgical site 402 may be performed at a lower radiation level than the initial scan. By way of example, FIG. 6 is an example diagram of an image 600 of a second three-dimensional image data set. The second three-dimensional image data set is based on a second scan of the surgical site 402 subsequent to the initial scan of the surgical site 402. The second scan of the surgical site 402 includes spinal anatomy and a surgical implant 604.

Figure 7:
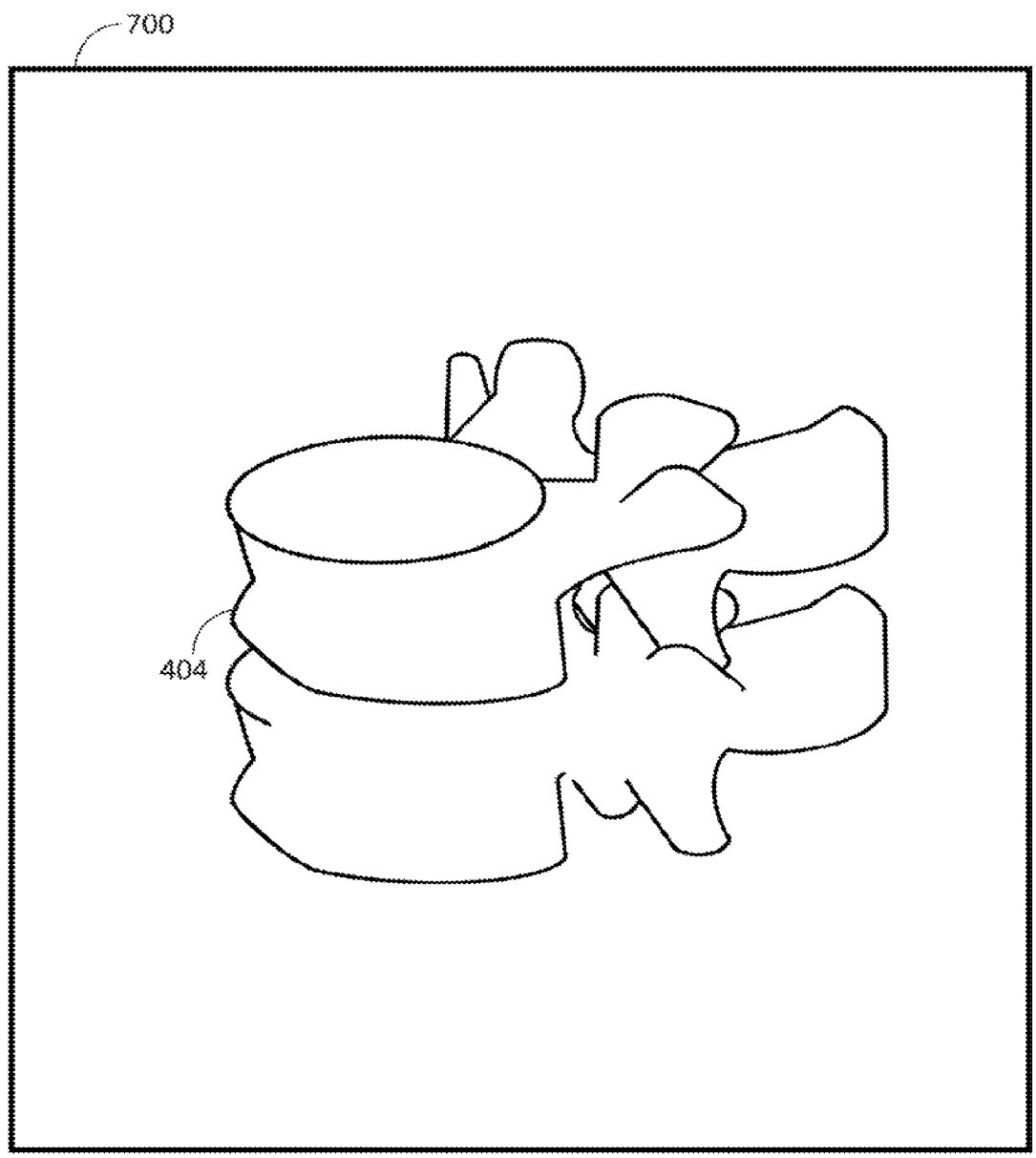
FIG. 7 illustrates an example diagram of another image, according to an example embodiment.

In one example, the processing device 122 is configured to receive the image 600 and register the segmented vertebral body 404 from the image 500 with the image 600. By way of example, FIG. 7 is an example diagram of the segmented vertebral body 404 from the image 500 to the image 600.

Figure 8:
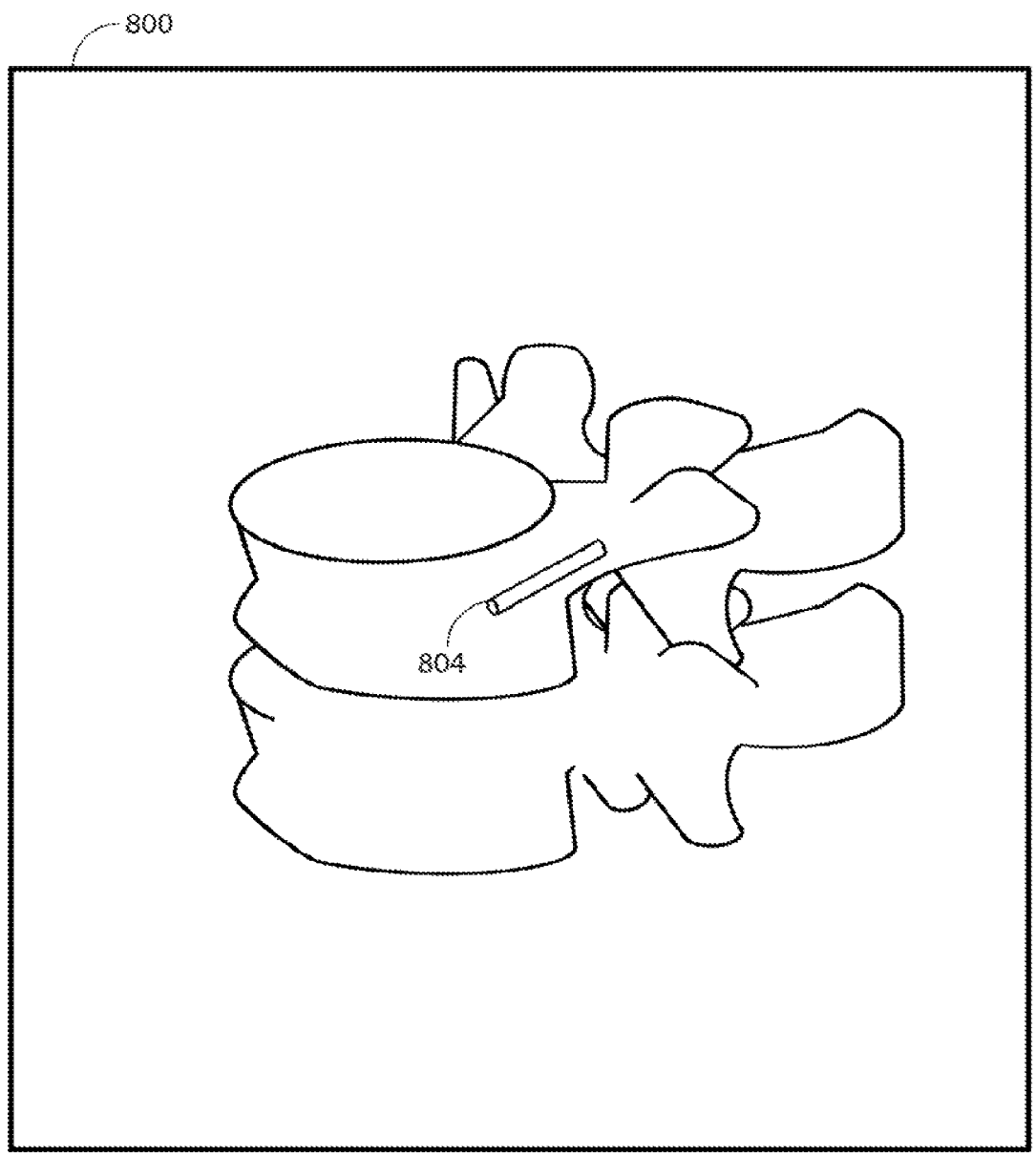
FIG. 8 illustrates an example diagram of another image, according to an example embodiment.

In one example, the processing device 122 is configured to determine a position of the surgical implant 604 based on the image 600 and a three-dimensional geometric model of the surgical implant 604. In one example, the processing device 122 is configured to overlay a virtual representation of the surgical implant 604 on the registered and segmented vertebral body 404. For example, FIG. 8 is an example diagram of an image 800 that includes the registered and segmented vertebral body 404 with the image 600 in addition to a virtual representation 804 of the surgical implant 604. In this example, a user may review the positioning of the surgical implant 604 with the benefit of the image 400 that based on an initial scan of the surgical site 402 at a high radiation level than the second scan of the surgical site in order to have a better representation of the surgical site while utilizing less radiation during the surgical procedure.

Figure 9:
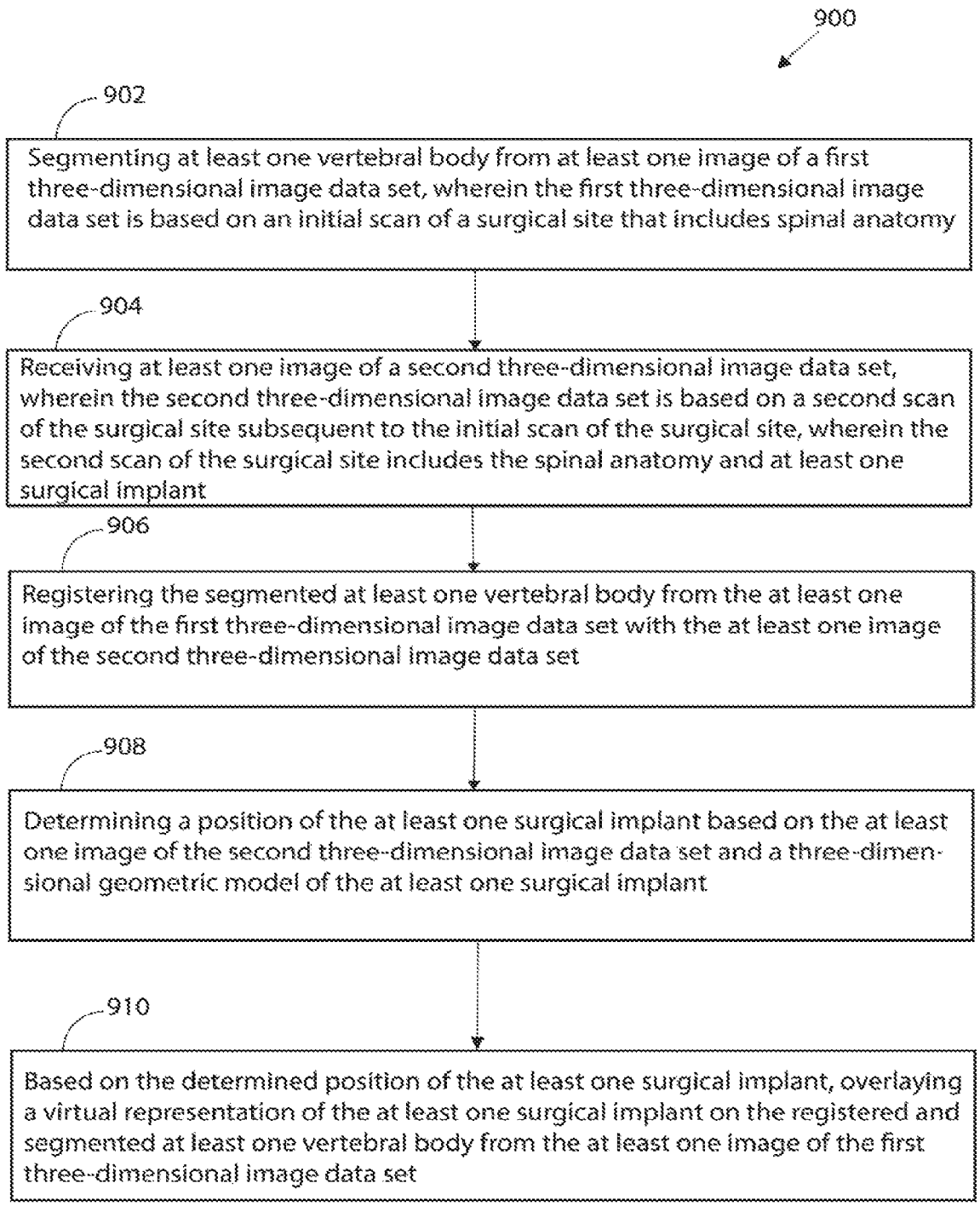
FIG. 9 illustrates a flow diagram of an example method for three-dimensional visualization during surgery, according to an example embodiment.

FIG. 9 is flow diagram of an example method for three-dimensional visualization during surgery, in accordance with at least one embodiment described herein. Although the blocks in each figure are illustrated in a sequential order, the blocks may in some instances be performed in parallel, and/or in a different order than those described therein. Also, the various blocks may be combined into fewer blocks, divided into additional blocks, and/or removed based upon the desired implementation.

As shown by block 902, the method 900 includes segmenting at least one vertebral body from at least one image of a first three-dimensional image data set, wherein the first three-dimensional image data set is based on an initial scan of a surgical site that includes spinal anatomy. In one example, the first three-dimensional image data set includes one or more of fluoroscopic images or computerized tomography scan images. In one example, the C-Arm 103 is used to capture an initial three-dimensional scan of the surgical site, as described above. By way of example, the surgical site includes spinal anatomy of a patient. In this example, the processing device 122 is configured to receive a three-dimensional image data set corresponding to the surgical site based on the captured initial three-dimensional scan. Continuing with this example, the processing device 122 is configured to segment at least one vertebral body from the received three-dimensional image data set.

In one scenario, the processing device 122 is configured to apply a fully convolutional network with a residual neural network to the received one or more images and segment one or more vertebral bodies from the one or more images of the spinal anatomy. In one example, given the segmented vertebral bodies, the vertebral levels are labeled semi-automatically. For example, a user indicates the level of the L5 vertebra on the segmented image. In this example, a three-dimensional connected component extraction algorithm is applied to label different vertebral regions. In one example, the isolated components smaller than a predetermined threshold are removed. In this example, a discrete marching cube algorithm is applied on each component, followed by a mesh smoothing process using a windowed sampling function applied in the frequency domain. This is implemented as an interpolation kernel performed on each voxel. Further, depending on what level has been defined by the user as the lower most vertebra, the remaining vertebrae are labeled in sequential order. In one example, the processing device 122 is configured to segment the at least one vertebral body from the at least one image of the first three-dimensional image data set is according to a deep neural network.

The three-dimensional image data set may also serve as a basis for planning of the surgery using manual or automated planning software. For example, a plan for placement of pedicle screws may be derived from use of a planning tool included in the planning software. Such planning software provides the surgeon with an understanding of the patient's anatomical orientation, the appropriate size of surgical instruments and implants, and proper trajectory for implants. According to some implementations, the system provides for the planning for pedicle screws, whereby the system identifies a desired trajectory in addition to the diameter and length for each pedicle screw in the surgical plan given the patient's anatomy and measurements. In one example, one or more images of the three-dimensional image data set may be displayed on a display (e.g., display device 126) and a representation of a plan for placement of pedicle screws may be overlaid on the one or more displayed images.

In one scenario, the surgeon may proceed to insert one or more implants based on the surgical plan. The surgeon may use a handheld tool or guide a robotic device (e.g., robotic device 140, robotic device 200) to insert the one or more implants. In this scenario, the tracking device 130 is configured to determine location data of the handheld tool or the robotic device as the one or more implants are inserted. The tracking device 130 is configured to provide the location data of the handheld tool or the robotic device to the processing device 122 for further processing.

As shown by block 904, the method 900 also includes receiving at least one image of a second three-dimensional image data set, wherein the second three-dimensional image data set is based on a second scan of the surgical site subsequent to the initial scan of the surgical site, wherein the second scan the surgical site includes the spinal anatomy and at least one surgical implant. In one example, the second three-dimensional image data set include one or more of fluoroscopic images or computerized tomography scan images. In one example, the second scan includes a plurality of surgical implants associated with the one vertebral body from at least the one image of the second three-dimensional image data set. In one example, once the one or more of the implants have been inserted, the C-Arm 103 is configured to capture a subsequent three-dimensional scan of the surgical site. In one example, the processing device 122 is configured to receive a three-dimensional image data set corresponding to the subsequent three-dimensional scan of the surgical site. In one example, the processing device 122 is configured to segment at least one vertebral body from the three-dimensional image data set corresponding to the subsequent three-dimensional scan of the surgical site, as described above.

As shown by block 906, the method 900 also includes registering the segmented at least one vertebral body from the at least one image of the first three-dimensional image data set with the at least one image of the second three-dimensional image data set. In one scenario, the processing device 122 is configured to compare one or more images corresponding to the subsequent three-dimensional scan to one or more images corresponding to segmented vertebral bodies from the initial three-dimensional scan in order to obtain an image registration. In one example, the processing device 122 is configured to register the segmented at least one vertebral body from the at least one image of the first three-dimensional image data set with the at least one image of the second three-dimensional image data set that includes one or more of a horizontal translation, a vertical translation, a rotation, and a scaling of the image information contained within the one vertebral body from the at least one image of the first three-dimensional image data set. In another example, the subsequent three-dimensional scan and the determined position from the tracking device 130 are compared. For example, when both the instrument/implant and the C-Arm are tracked, the location of the anatomy relative to the imaging source and the location of the equipment relative to the imaging source are known. This information can thus be used to quickly and interactively ascertain the location of the equipment or hardware relative to the anatomy. In one example, if a position of one or more vertebral bodies has been adjusted during the surgical procedure, the processing device 122 is configured to create a new virtual scan of the segmented vertebral bodies based on at least a current position of the one or more vertebral bodies.

In one example, the processing device 122 is configured to find the best fit of the segmented vertebral bodies from the initial scan with one or more images from the subsequent scan according to a predetermined correlation score. Various algorithms may be employed that may be dependent on various factors, such as the number of images in each of the image data sets, the size and speed of the computer processor or graphics processor performing the algorithm calculations, the time allotted to perform the computations, and the size of the images being compared. In one approach, comparisons are made between pixels at predetermined locations described above in a grid pattern throughout 4D space. In one approach, comparisons are made between pixels at predetermined locations described above in a grid pattern throughout 6D space. In another heuristic approach, pixel comparisons can be concentrated in regions of the images believed to provide a greater likelihood of a relevant match. These regions may be "pre-seeded" based on knowledge from a grid or PCA search, data from a tracking system (e.g., tracking device 130), or location data from a DICOM file or the equivalent. In one example, the processing device 122 may be configured to use captured navigation locations from where a final screw placed and a rough location in a metal artifact scan to simplify an algorithm's search criteria.

As shown by block 908, the method 900 also includes determining a position of the at least one surgical implant based on the at least one image of the second three-dimensional image data set and a three-dimensional geometric model of the at least one surgical implant. In one example, the processing device 122 is configured to use a three-dimensional geometric model of the implants to identify the best correlated final position of each implant in one or more images corresponding to the subsequent scan. The three-dimensional geometric model may include multiple measurements of the implant that can be used for identification by the processing device 122. For example, the processing device 122 may use the length and diameter of a pedicle screw to identify the best correlated final position of each pedicle screw in one or more images corresponding to the subsequent scan.

As shown by block 910, the method 900 also includes based on the determined position of the at least one surgical implant, overlaying a virtual representation of the at least one surgical implant on the registered and segmented at least one vertebral body from the at least one image of the first three-dimensional image data set. In one example, the processing device 122 is configured to overlay one or more three-dimensional geometric models on one or more images corresponding to segmented vertebral bodies from the initial three-dimensional scan. In this example, the processing device 122 is configured to use i) the best fit of the segmented vertebral body from the initial scan with one or more images from the subsequent scan according to the predetermined correlation score and ii) the best correlated final position of each implant in the one or more images corresponding to the subsequent scan, as described above, to display an image of a given segmented vertebral body with an overlaid virtual representation of the implant. Continuing with this example, the displayed image corresponds to an image of the inserted implant according to the subsequent three-dimensional scan captured via the C-Arm 103. In one example, the processing device 122 is configured to display a three-dimensional image including the inserted implant from the subsequent three-dimensional scan and a three-dimensional image from the initial three-dimensional scan that also includes an overlay of the virtual representation of the implant so that a surgeon can determine if the final implant placement is satisfactory to proceed with any remaining steps of the surgical procedure.

Figure 10:
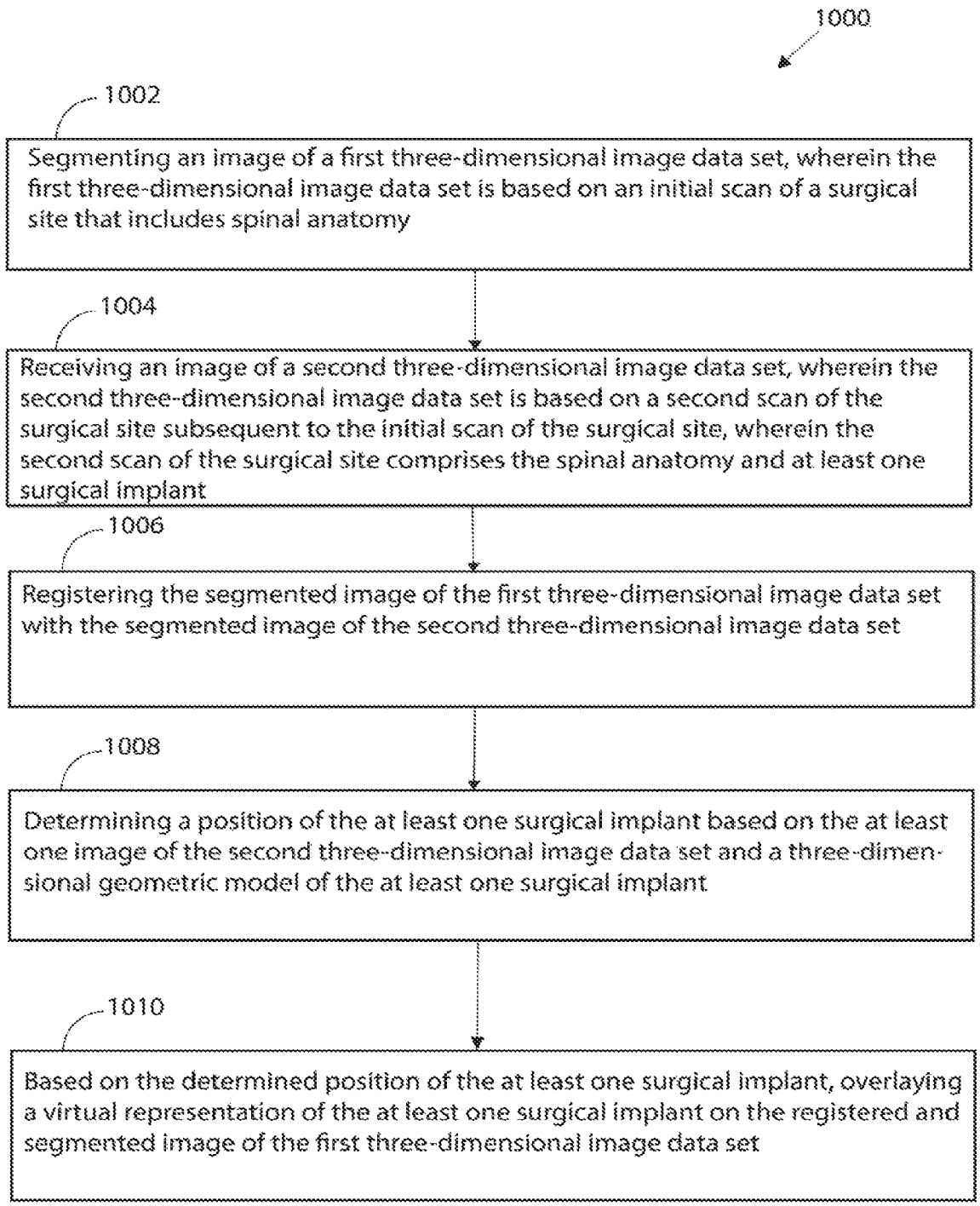
FIG. 10 illustrates a flow diagram of another example method for three-dimensional visualization during surgery, according to an example embodiment.

FIG. 10 is flow diagram of an example method for three-dimensional visualization during surgery, in accordance with at least one embodiment described herein. Although the blocks in each figure are illustrated in a sequential order, the blocks may in some instances be performed in parallel, and/or in a different order than those described therein. Also, the various blocks may be combined into fewer blocks, divided into additional blocks, and/or removed based upon the desired implementation.

As shown by block 1002, the method 1000 includes segmenting an image of a first three-dimensional image data set, wherein the first three-dimensional image data set is based on an initial scan of a surgical site that includes spinal anatomy. In one example, segmenting the image of the first three-dimensional image data set is based on user input. In another example, the user input includes an input received via a touch screen display. For example, the display device 126 may include touch screen display as displays 123 and 124.

As shown by block 1004, the method 1000 also includes receiving an image of a second three-dimensional image data set, wherein the second three-dimensional image data set is based on a second scan of the surgical site subsequent to the initial scan of the surgical site, wherein the second scan of the surgical site comprises the spinal anatomy and at least one surgical implant. In one example, the first three-dimensional image data set and the second three-dimensional image data set include one or more of fluoroscopic images or computerized tomography scan images. In another example, the first three-dimensional image data set and the second three-dimensional image data set include fluoroscopic images and the initial scan of the surgical site is associated with a higher radiation level than the second scan of the surgical site. In one example, the second scan includes a plurality of surgical implants associated with the one vertebral body from at least the one image of the second three-dimensional image data set.

As shown by block 1006, the method 1000 also includes registering the segmented image of the first three-dimensional image data set with the segmented image of the second three-dimensional image data set. In one example, registering the segmented image of the first three-dimensional image data set with the image of the second three-dimensional image data set includes one or more of a horizontal translation, a vertical translation, a rotation, and a scaling of the image information contained within the one vertebral body from the at least one image of the first three-dimensional image data set.

As shown by block 1008, the method 1000 also includes determining a position of the at least one surgical implant based on the at least one image of the second three-dimensional image data set and a three-dimensional geometric model of the at least one surgical implant.

As shown by block 1010, the method 1000 also includes based on the determined position of the at least one surgical implant, overlaying a virtual representation of the at least one surgical implant on the registered and segmented image of the first three-dimensional image data set.

The flow diagrams of FIGS. 9 and 10 shows the functionality and operation of two possible implementations of the present embodiment. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example.

Alternatively, each block in FIGS. 9 and 10 may represent circuitry that is wired to perform the specific logical functions in the process. Illustrative methods, such as the ones shown in FIGS. 9 and 10, may be carried out in whole in or in part by a component or components in the cloud. However, it should be understood that the example methods may instead be carried out by other entities or combinations of entities (i.e., by other computing devices and/or combination of computer devices), without departing from the scope of the invention. For example, functions of the methods of FIGS. 9 and 10 may be fully performed by a computing device (or components of a computing device such as one or more processors), or may be distributed across multiple components of the computing device, across multiple computing devices, and/or across a server.

Figure 11:
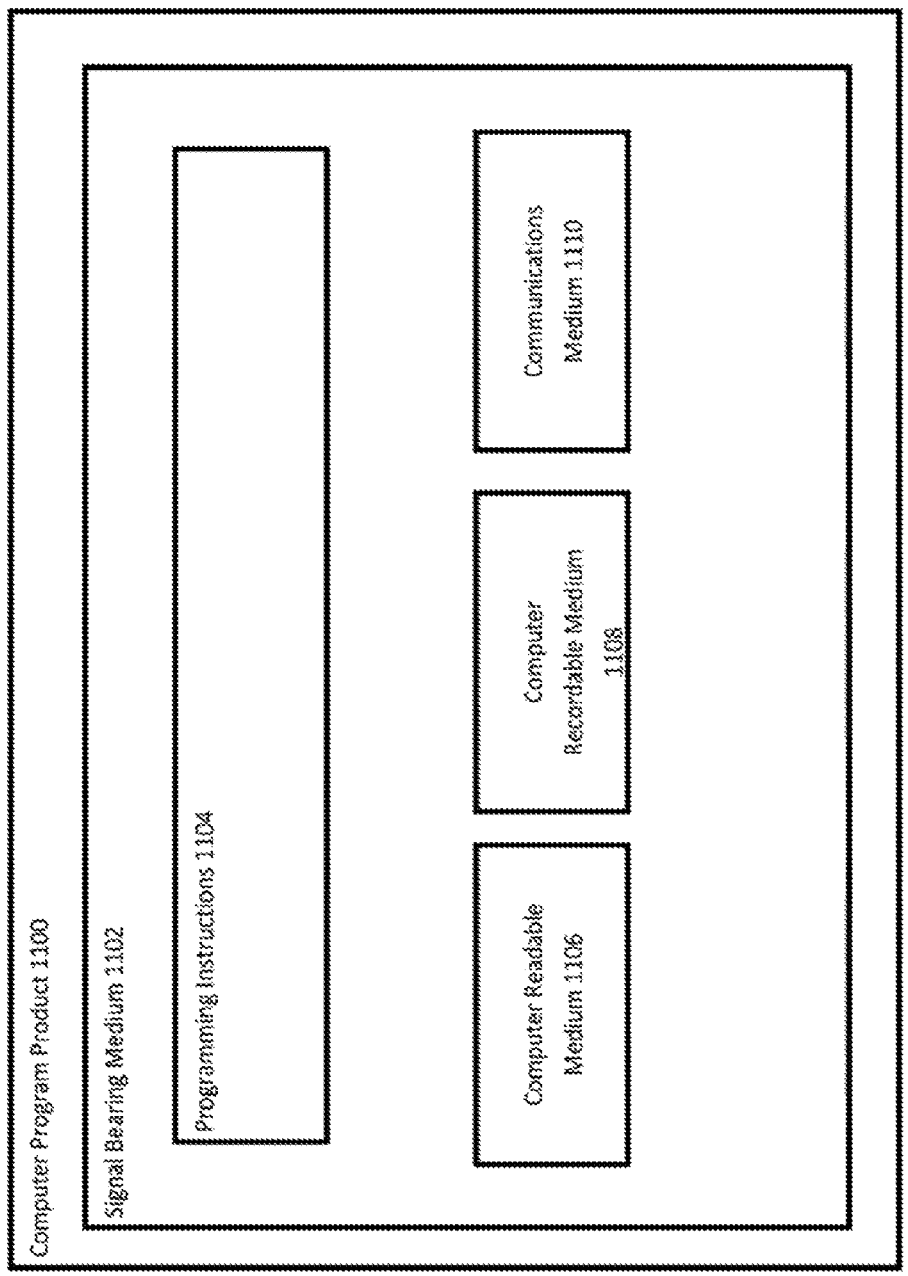
FIG. 11 illustrates an example computer readable medium, according to an example embodiment.

FIG. 11 depicts an example computer readable medium configured according to an example embodiment. In example embodiments, an example system may include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g., functions of the robotic device 140, robotic device 200, processing device 122, computing device 300, etc.) may be implemented by computer program instructions encoded on a computer readable storage media in a machine-readable format, or on other media or articles of manufacture. FIG. 11 is a schematic illustrating a conceptual partial view of an example computer program product that includes a computer program for executing a computer process on a computing device, arranged according to at least some embodiments disclosed herein.

In one embodiment, an example computer program product 1100 is provided using a signal bearing medium 1102. The signal bearing medium 1102 may include one or more programming instructions 1104 that, when executed by one or more processors may provide functionality or portions of the functionality described above with respect to FIGS. 1-10. In some examples, the signal bearing medium 1102 may be a computer-readable medium 1106, such as, but not limited to, a hard disk drive, a Compact Disc (CD), a Digital Video Disk (DVD), a digital tape, memory, etc. In some implementations, the signal bearing medium 1102 may be a computer recordable medium 1108, such as, but not limited to, memory, read/write (R/W) CDs, R/W DVDs, etc. In some implementations, the signal bearing medium 1102 may be a communication medium 1110 (e.g., a fiber optic cable, a waveguide, a wired communications link, etc.). Thus, for example, the signal bearing medium 1102 may be conveyed by a wireless form of the communications medium 1110.

The one or more programming instructions 1104 may be, for example, computer executable and/or logic implemented instructions. In some examples, a computing device may be configured to provide various operations, functions, or actions in response to the programming instructions 1104 conveyed to the computing device by one or more of the computer readable medium 1106, the computer recordable medium 1108, and/or the communications medium 1110.

The computer readable medium 1106 may also be distributed among multiple data storage elements, which could be remotely located from each other. The computing device that executes some or all of the stored instructions could be an external computer, or a mobile computing platform, such as a smartphone, tablet device, personal computer, wearable device, etc. Alternatively, the computing device that executes some or all of the stored instructions could be remotely located computer system, such as a server.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

What is claimed is:

1. A system for generating a display of an image of a patient's internal anatomy during a surgical procedure comprising:

a display and a processor in communication with the display, wherein the processor is configured to:

segmenting at least one vertebral body from a first three dimensional image, wherein the first three-dimensional image is based on an initial scan of a surgical site that includes spinal anatomy, to provide a segmented at least one vertebral body;

receiving a second three-dimensional image, wherein the second three-dimensional image is based on a second scan of the surgical site subsequent to the initial scan of the surgical site, wherein the second scan of the surgical site includes the spinal anatomy and at least one surgical implant;

registering the segmented at least one vertebral body from the first three-dimensional image with image data of the second three-dimensional image, to provide a registered and segmented at least one vertebral body from the first three-dimensional image;

determining a position of the at least one surgical implant based on the image data of the second three-dimensional image and a three-dimensional geometric model of the at least one surgical implant, to provide a determined position of the at least one surgical implant; and based on the determined position of the at least one surgical implant, overlaying a virtual representation of the at least one surgical implant on the registered and segmented at least one vertebral body from the first three-dimensional image.

2. The system of claim 1, wherein the first three-dimensional image and the second three-dimensional image include computerized tomography scan images.

3. The system of claim 2, wherein the initial scan of the surgical site is associated with a higher radiation level than the second scan of the surgical site.

4. The system of claim 1, wherein the second scan includes a plurality of surgical implants associated with the at least one vertebral body from at least the one image of the first three-dimensional image.

5. The system of claim 1, wherein segmenting the at least one vertebral body from the first three-dimensional image is determined according to a deep neural network.

6. The system of claim 1, wherein registering the segmented at least one vertebral body from the first three-dimensional image with the second three-dimensional image includes one or more of a horizontal translation, a vertical translation, a rotation, and a scaling of image information contained within the at least one vertebral body from the first three-dimensional image.

* * * * *